(12) United States Patent
Furlan et al.

(10) Patent No.: US 7,153,970 B2
(45) Date of Patent: Dec. 26, 2006

(54) HIGH PURITY AMLODIPINE BENZENESULFONATE AND A PROCESS FOR ITS PREPARATION

(75) Inventors: Borut Furlan, Ljubljana (SI); Marijan Resnik, Menges (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 26 days.

(21) Appl. No.: 10/482,603

(22) PCT Filed: Jul. 5, 2002

(86) PCT No.: PCT/IB02/02668

§ 371 (c)(1),
(2), (4) Date: Dec. 23, 2003

(87) PCT Pub. No.: WO03/004025

PCT Pub. Date: Jan. 16, 2003

(65) Prior Publication Data

US 2004/0176606 A1    Sep. 9, 2004

(30) Foreign Application Priority Data

Jul. 6, 2001  (SI) .................................. P-479/01

(51) Int. Cl.
*C07D 213/80* (2006.01)
*C07D 213/803* (2006.01)
*A61K 31/4418* (2006.01)

(52) U.S. Cl. ........................... 546/321; 514/356

(58) Field of Classification Search ............... 546/321; 514/356
See application file for complete search history.

(56) References Cited

U.S. PATENT DOCUMENTS

| | | | |
|---|---|---|---|
| 4,572,909 A | 2/1986 | Campbell et al. | 514/356 |
| 4,879,303 A | 11/1989 | Davison et al. | 514/356 |
| 5,389,654 A | 2/1995 | Furlan et al. | 514/356 |
| 5,438,145 A | 8/1995 | Furlan et al. | 546/321 |
| 6,046,337 A | 4/2000 | Bózsing et al. | 546/321 |
| 6,596,874 B1 | 7/2003 | Fischer et al. | 546/321 |
| 2002/0045648 A1 | 4/2002 | Chahwala et al. | 514/355 |

FOREIGN PATENT DOCUMENTS

| | | |
|---|---|---|
| EP | 0 089 167 | 10/1986 |
| EP | 0 244 944 | 1/1990 |
| EP | 0 599 220 | 8/1996 |
| EP | 0 902 016 | 3/1999 |
| EP | 1 181 932 | 2/2002 |
| WO | 99/52873 | 10/1999 |
| WO | 01/02360 | 1/2001 |

OTHER PUBLICATIONS

Zmitck et al., "Sources of Impurities—Investigation of 4-(2-Chlorophenyl)-3-Ethoxycarbonyl-5-Methoxycarbonyl-6-Methyl-2-[(2-Phthalimidoethoxy)Methyl]-1,4-Dihydropyridine Traces Formation During the Synthesis of Amlodipine Besylate", Acta Chim. Slov., vol. 47, pp. 63-68 (2000).

*Primary Examiner*—Bernard Dentz
(74) *Attorney, Agent, or Firm*—John D. Thallemer

(57) ABSTRACT

3-ethyl 5-methyl (+/−) 2-[(2-aminoethoxy)methyl]-4-(2-chlorophenyl)-1,4-dihydro-6-methyl-3,5-pyridinedicarboxylate benzenesulfonate, containing overall impurities of significantly less than 0.3% is disclosed, as well as process for its preparation, according to which substance of 3-ethyl 5-methyl (+/−) 2-[2-(N-trialkylamino)ethoxymethyl]-4-(2-chlorophenyl)-1,4-dihydro-6-methyl-3,5-pyridinedicarboxylate is converted with benzenesulfonic acid in ethanol solution, at a temperature between 20° C. and reflux temperature, followed by isolation and purification of 3-ethyl 5-methyl (+/−) 2-[(2-aminoethoxy)methyl]-4-(2-chlorophenyl)-1,4-dihydro-6-methyl-3,5-pyridinedicarboxylate benzenesulfonate. Amlodipine benzenesulfonate is useful as an antiishemic and antihypertensive agent.

10 Claims, No Drawings

HIGH PURITY AMLODIPINE BENZENESULFONATE AND A PROCESS FOR ITS PREPARATION

This application is a national stage entry of PCT/IB02/02668 filed Jul. 5, 2002.

The present invention belongs to the field of heterocyclic compounds in chemistry and pharmaceutical industry, and relates to high purity amlodipine benzenesulfonate, containing overall impurities of significantly less than 0.3%, as well as to a novel process for its preparation.

Amlodipine benzenesulfonate is an effective agent in blocking calcium canals and is useful as antiishemic and antihypertensive agent.

There is a need of high purity amlodipine benzenesulfonate, by a novel process for its preparation, obtaining desirable the substance in an easy performable manner, with high yield and high purity.

Amlodipine is a generic name for 3-ethyl 5-methyl (+/−)-2-(2-aminoethoxy)methyl]-4-(2-chlorophenyl)-1,4-dihydro-6-methyl-3,5-pyridinedicarboxylate, and was disclosed as a novel substance in the European Patent EP-B-00 89 167 as a useful antiishemic and antihypertensive agent. Also, pharmaceutically acceptable amlodipine acid addition salts were described, among which, maleate salt is particularly suitable.

Amlodipine in a common base form may be prepared by the methods disclosed in the European Patent EP-B-00 89 167. According to these methods, amlodipine base is prepared from an amlodipine precursor, that is a 1,4-dihydropyridine derivative, which has an amino group in position 2, protected with selected protecting groups, in such a manner that these amino protecting groups are removed from protected 1,4-dihydropyridine derivative. In case that the amino group is protected with a benzyl group, the protecting group is removed by catalytic hydrogenation with a palladium catalyst in a dissolving agent, such as methanol and at room temperature. In a particularly suitable process, wherein the 1,4-dihydropyridine derivative amino protecting group is preferably a phthaloyl protecting group, this derivative amino protecting group is removed by converting amino protected 1,4-dihydropyridine derivative in an alkaline medium with a) primary amine, such as methylamine, b) hydrazine hydrate or c) alkali metal hydroxide, followed by treatment with hydrochloric and sulfuric acid. The resulting amlodipine base is, if desired, converted to a pharmaceutically acceptable acid addition salt thereof.

Also, a process for preparing amlodipine base from amlodipine precursors, having an azide group in position 2, which reduction yields amlodipine base, was disclosed in European Patent EP-B-00 89 167, and if desired, the substance is converted to a pharmaceutically acceptable acid addition salt thereof.

The yields of said amlodipine precursor, which was prepared according to the well known Hantzsch method for preparing asymmetric, 1,4-dihydropyridine diesters, are relatively low. The process wherein a phthaloyl group was used for protecting amino groups, require the use of toxic agents, which are not allowed in desired pharmaceutically acceptable acid addition salt. The toxic and cancerous chemical compounds are methylamine, and particularly hydrazinhydrate, Additionally, the reduction of 1,4-dihydropyridine azide derivative gives low yields of the desired chemical compound and, moreover, work with azide chemical compounds is inconvenient, because of known explosive azide structure.

European Patent EP-B-0 244 944 discloses a novel amlodipine benzenesulfonic (benzylate) salt and pharmaceutical forms thereof. This salt is particularly suitable for preparing amlodipine pharmaceutical forms for its own good water solubility, high stability, nonhygroscopicity and good properties for manufacturing. In accordance with the patent description, amlodipine benzenesulfonate salt was prepared by converting amlodipine base substance with benzenesulfonic acid or with ammonium benzenesulfonate in the dissolving inert agent, such as industry methylated ethanol.

European Patent EP-B-0 599 220 discloses a process for preparing amlodipine benzenesulfonate, according to which converting new amlodipine precursor was performed, that is chemically 3-ethyl 5-methyl (+/−)2-[2-(N-tritylamino)-ethoxymethyl]-4-(2-chlorophenyl)-1,4-dihydro-6-methyl-3,5-pyridinedicarboxylate, prepared via Hantzsch method, with benzenesulfonic acid in methanol or water-methanol medium, at a temperature between 20° C. and reflux temperature, followed by amlodipine benzenesulfonate salt isolation and purification. The process is characterized by good overall yields of the desired chemical compound, avoidance of work with some toxic and cancerous chemicals, as well as avoidance of preparing and isolating amlodipine base required in the process, disclosed in European Patents EP-B-00 89 167 and EP-B-00 244 944. According to the scope of the invention disclosed in Patent EP-B-0 599 220, amlodipine base is generally not obtained by the process of substance converting.

The object of the invention is to provide high purity amlodipine benzenesulfonate, containing overall impurities of significantly less than 0.3% and a process for its preparation, according to which high yield amlodipine benzenesulfonate is obtained and can easily be isolated from the reaction mixture. These and other features including various preferred embodiments will become more apparent with reference to the disclosure herein.

A further object of the present invention is to provide pharmaceutical preparations, such as tablets, capsules and sterile water solutions, comprising amlodipine benzenesulfonate with overall impurities of significantly less than 0.3%, together with pharmaceutically acceptable diluents and/or carriers. In accordance with the present invention, tablets containing amlodipine benzenesulfonate in combination with excipients are provided. Preferred compositions contain amlodipine benzenesulfonate in combination with thickening agent, such as microcrystalline cellulose, additives for tablet shine achieving, such as anhydrous dibasic calcium phosphate, desintegrant, such as sodium glycolate starch and lubricant, such as magnesium stearate, according to the present invention. These and other features including various preferred embodiments will become more apparent with reference to the disclosure herein.

The present invention is also concerned with the use of amlodipine benzenesulfonate, containing overall impurities of significantly less than 0.3% for the manufacture of a medicament for the treatment of heart diseases, particularly angina or hypertension.

Unexpectedly, it was found that greater yields of high purity amlodipine benzenesulfonate, readily isolated as the desired substance from a reaction mixture after substance converting had been completed in accordance with the process disclosed in European Patent EP-B-0 599 220 were obtained, if the process according to the present invention occurs in ethanol medium, instead of methanol or water methanol medium.

At first, the reaction of condensation 1,4-dihydropyridine, prepared via the Hantzsch method for preparing asymmetric diesters, with ethyl 4-2-(N-tritylamino)ethoxy acetoacetate, methyl-(E)-3-amino crotonate and 2-chlorobenzaldehyde, in ethanol medium, at reaction mixture reflux temperature provides 3-ethyl 5-methyl (+/−)2-[2-(N-tritylamino)-ethoxymethyl]-4-(2-chlorophenyl)-1,4-dihydro-6-methyl-3,5-pyridinedicarboxylate, without isolation from ethanol reaction mixture, was carried out, followed by converting the substance with benzenesulfonic acid in ethanol medium, at a temperature between 20° C. and reflux temperature. After the converting of the substance had been completed, the resulting amlodipine benzenesulfonate was isolated and purified, including stirring after complete substance converting was achieved, at a temperature below 0° C., most preferred at about −10° C., to remove triphenylmethyl ethyl ether, which was separated after substance converting.

The resultant amlodipine benzenesulfonate, according to the present invention has high purity and contains overall impurities of significantly less than 0.3%.

2-chlorobenzaldehyde and methyl (E)-3-aminocrotonate, required in the Hantzsch synthesis of asymmetric 1,4-dihydropyridine esters, are commercially available, while ethyl 4-[2-(N-tritylamino)-ethoxy]acetoacetate was prepared in a manner, disclosed in European Patent EP-B-0 599 220, such as illustrated in the example below.

The present invention is exemplified, but not limited to the following examples:

EXAMPLE 1

In the first reactor, 10.7 mol (0.428 kg) 60% sodium hydride in mineral oil and 2.4 litre of anhydrous tetrahydrofuran are placed. In the second reactor, a solution of 4.4 mol (1.337 kg) N-trityl-2-aminoethanol (prepared such as described in European Patent EP-B-0-599 220) in 3.4 litre anhydrous tetrahydrofuran is placed. To the sodium hydride suspension, a solution of N-trityl-2-aminoethanol while vigorous stirring, and in a stream of dry nitrogen, at a temperature between 20° C. and 30° C. is slowly added (2 to 2.5 hours). Then, reaction mixture is further stirred for another 2 hours, at a temperature between 25° C. and 30° C.

In the third reactor a mixture of 4.45 mol (0.773 kg) ethyl-4-chloroacetoacetate and 0.9 litre of anhydrous tetrahydrofuran is prepared, and cooled to 0° C. to 5° C. A solution of ethyl-4-chloroacetoacetate is slowly added (3 to 4 hours), while vigorous stirring, and in a stream of dry nitrogen, at a temperature between 0° C. and 10° C. (most preferred between 4° C. and 8° C.) to the reaction mixture of N-trityl-2-aminoethanol. Then, the reaction mixture is stirred for five hours at a temperature between 5° C. and 10° C., and for 15 hours at a temperature between 20° C. and 30° C., all the time under the softly dry nitrogen flow.

The reaction in the stream of nitrogen is quenched by adding ethanol (0.45 litre) and demineralized water (14 litre). The nitrogen flow is stopped. The reaction mixture is neutralized with concentrated hydrochloric acid to a pH value of 7 (acid consumption was 0.25 litre), then was stirred for another 20 minutes at 25° C. to 35° C., and each of the layers is separated.

The upper organic layer is diluted with 5.6 litre ethylacetate, 0.25 kg sodium chloride is added, and is washed with 6.56 litre demineralized water. The aqueous phase is separated, and again washed with 6.5 litre demineralized water, with addition of 0.25 kg sodium chloride. The organic phase is concentrated on a rotation vacuum evaporizer, and a remaining oil is dissolved in 1.7 litre of absolute ethanol, in a temperature range between 35° and 45° C. The ethanol solution is evaporated in vacuo, and a remaining oil (1.95 kg) is again dissolved in 2.7 litre absolute ethanol. The resulting solution is further used in a process according to the present invention.

An ethanol solution of ethyl-4-(2-N-tritylamino) ethoxy acetoacetate, prepared in accordance with above, 3.9 litre of absolute ethanol, and 3.72 mol (0.429 kg) of methyl(E)-3-aminocrotonate is placed in the reactor. The reaction mixture is heated to 45° C. to 55° C. and stirred at that temperature for 30 minutes. Then, to a reaction mixture additional 3.70 mol (0.520 kg) 2-chlorobenzaldehyde is added, warmed up to the reaction mixture reflux temperature, and heated at reflux temperature for 20 hours.

In the other reactor, a solution of technic 95% benzenesulfonic acid (3.86 mol, 0.643 kg) in 0.8 litre of absolute ethanol is prepared. The ethanol solution is slowly added (1.5 hours) at reflux temperature into the reaction mixture, the reaction mixture is heated at reflux temperature for additional 1 hour, then is cooled to 0° C. to −10° C., and stirred at that temperature another three hours. The precipitate (1.1 kg) of triphenylmethyl ethyl ether, is isolated and filtered, and the filtrate is concentrated in vacuo to a slurry residue (2.6 kg).

Demineralized water (7.2 litre) is added to the slurry residue mixture, heated to 40° C. to 50° C., and an aqueous phase is separated. The procedure is repeated two times, then another 4 litre of the mixture of toluene and n-heptane (1:1) and 4 litre of demineralized water is added; then the mixture is heated to 60° C. to 70° C., and placed into a continual extractor for extraction with specifically light solvents. In the extraction sample, toluene and n-heptane mixture (1:1) is placed. The slurry mixture (three-phase system: resin-water-toluene/n-heptane) is continually extracted for 24 hours, maintaining extractor temperature between 50° C. and 60° C. After the extraction has been completed, the toluene/n-heptane phase and the aqueous phase are separated and the residue is concentrated in vacuo. 1.35 kg of a slurry of the solid amorphous residue is obtained.

Ethylacetate (3.0 litre) and water (0.1 litre) is added to the evaporated residue, heated to be dissolved (40° C. to 50° C.), and cooled to −10° C. to −15° C. At this temperature, reaction mixture is stirred for 20 hours, the obtained precipitate is filtered and washed with 0.5 litre of cold ethylacetate. 1.05 kg of wet precipitate is obtained.

Again, fresh ethylacetate (2.1 litre) and water (0.08 litre) is added to the wet precipitate; the reaction mixture is heated to be dissolved (50° C. to 60° C.), and the solution is cooled to −10° C. to −15° C. At this temperature, the reaction mixture is stirred for 10 hours, the resulting precipitate is filtered and washed with 0.5 litre of cold ethylacetate. 0.85 kg of wet precipitate is obtained.

The wet precipitate is placed into a reactor, 7.2 litre of demineralized water is added and the reaction mixture is heated to be dissolved (50° C. to 60° C.). The composition is cooled very slowly to 0° C. to 10° C. (up to 10 hours), and resulting crystals are filtered and dried in vacuo. 0.57 kg of dry crystallized amlodipine benzenesulfonate is obtained.

The product is crystallized from methanol (1.1 litre) and the resulting crystals are filtered (0.45 kg of wet crystals), and then, the crystalisation from methanol (0.8 litre) is repeated. After the filtration and vacuum drying 0.38 kg (0.67 mol) of white crystals of high purity amlodipine benzenesulfonate, containing overall impurities of significantly less than 0.3% are obtained (as established by HPLC method). The melting point of the obtained amlodipine benzenesulfonate is 201.0° C.

The invention claimed is:

1. A process for making 3-ethyl 5-methyl (+/−) 2-[(2-aminoethoxy)methyl]-4-(2-chlorophenyl)-1,4-dihydro-6-methyl-3,5-pyridinedicarboxylate benzenesulfonate (amlodipine benzenesulfonate) comprising reacting 3-ethyl 5-methyl (+/−) 2-[2-(N-tritylamino)ethoxymethyl]-4-(2-chlorophenyl)-1,4-dihydro-6-methyl-3,5-pyridinedicarboxylate with benzenesulfonic acid in the presence of ethanol media, at a temperature of from about 20° C. to a reflux temperature, followed by isolation and purification of amlodipine benzenesulfonate as a product thereof.

2. The process according to claim 1, wherein the 3-ethyl 5-methyl (+/−) 2-[(2-aminoethoxy)methyl]-4-(2-chlorophenyl)-1,4-dihydro-6-methyl-3,5-pyridinedicarboxylate benzenesulfonate (amlodipine benzenesulfonate) product contains overall impurities of less than 0.3%.

3. A process for making a pharmaceutical composition containing amlodipine benzenesulfonate, comprising the steps of claim 2 and subsequently combining the amlodipine benzenesulfonate with a pharmaceutically acceptable diluent or carrier.

4. In a method for making 3-ethyl 5-methyl (±) 2-[(2-aminoethoxy)methyl]-4-(2-chlorophenyl)-1,4-dihydro-6-methyl-3,5-pyridinedicarboxylate benzenesulfonate (amlodipine benzenesulfonate) by contacting 3-ethyl 5-methyl (±) 2-[-(N-tritylamino)ethoxymethyl]-4-(2-chlorophenyl)-1,4-dihydro-6-methyl-3,5-pyridinedicarboxylate with benzenesulfonic acid, the improvement comprising performing the contacting in a media containing ethanol at a temperature of from about 20° C. to a reflux temperature to produce a reaction mixture followed by isolation and purification of amlodipine benzenesulfonate from the reaction mixture.

5. The method of claim 4, wherein the steps of isolating and purifying amlodipine benzenesulfonate further comprise stirring at a temperature below about 0° C. to remove any triphenylmethyl methyl ether from the reaction mixture.

6. The method of claim 4, wherein the contacting step is performed substantially at a reflux temperature.

7. The method of claim 5, wherein the stirring comprises stirring at a temperature of about −10° C.

8. The method of claim 4, wherein the reaction mixture is in the form of a slurry residue and the amlodipine benzenesulfonate is extracted from the slurry residue using a mixture comprising toluene, n-heptane, and water, whereafter a substantially solid amorphous form of the amlodipine benzenesulfonate is obtained.

9. The method of claim 8, wherein the substantially solid amorphous form of the amlodipine benzenesulfonate is dissolved in a mixture comprising ethyl acetate and water and the resulting composition is cooled to a temperature ranging from about −10° C. to about −15° C. and stirred at this temperature to obtain a precipitate of ambodipine benzenesulfonate.

10. The method of claim 9, wherein the precipitate of amlodipine benzenesulfonate is dissolved in water and the resulting aqueous mixture cooled slowly to a temperature ranging from about 0° to about 10° C., whereupon crystals of amlodipine benzenesulfonate are formed contaming overall impurities of significantly less than 0.3%.

* * * * *

UNITED STATES PATENT AND TRADEMARK OFFICE
CERTIFICATE OF CORRECTION

PATENT NO. : 7,153,970 B2 Page 1 of 1
APPLICATION NO. : 10/482603
DATED : December 26, 2006
INVENTOR(S) : Furlan et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (26) days Delete the phrase "by 26" and insert -- by 0 days --

Signed and Sealed this

Eighteenth Day of November, 2008

JON W. DUDAS
*Director of the United States Patent and Trademark Office*

UNITED STATES PATENT AND TRADEMARK OFFICE
CERTIFICATE OF CORRECTION

PATENT NO. : 7,153,970 B2 Page 1 of 1
APPLICATION NO. : 10/482603
DATED : December 26, 2006
INVENTOR(S) : Furlan et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (26) days Delete the phrase "by 26" and insert -- by 0 days --

Signed and Sealed this

Twenty-fifth Day of November, 2008

JON W. DUDAS
*Director of the United States Patent and Trademark Office*